United States Patent
Ha et al.

(10) Patent No.: US 9,301,681 B2
(45) Date of Patent: Apr. 5, 2016

(54) OPHTHALMIC APPARATUS, AND TREATMENT SITE MEASURING METHOD FOR THE APPARATUS

(71) Applicant: LUTRONIC CORPORATION, Goyang (KR)

(72) Inventors: Tae Ho Ha, Goyang (KR); Ki Chan Kim, Incheon (KR)

(73) Assignee: LUTRONIC CORPORATION, Goyang (KR)

( * ) Notice: Subject to any disclaimer, the term of this patent is extended or adjusted under 35 U.S.C. 154(b) by 0 days.

(21) Appl. No.: 14/414,700

(22) PCT Filed: Jul. 15, 2013

(86) PCT No.: PCT/KR2013/006326
§ 371 (c)(1),
(2) Date: Jan. 13, 2015

(87) PCT Pub. No.: WO2014/011014
PCT Pub. Date: Jan. 16, 2014

(65) Prior Publication Data
US 2015/0173611 A1    Jun. 25, 2015

(30) Foreign Application Priority Data

Jul. 13, 2012 (KR) .......................... 10-2012-0076782

(51) Int. Cl.
| | |
|---|---|
| A61B 3/10 | (2006.01) |
| A61B 3/12 | (2006.01) |
| A61B 3/00 | (2006.01) |
| A61B 3/14 | (2006.01) |
| G06T 7/00 | (2006.01) |

(52) U.S. Cl.
CPC ................ *A61B 3/12* (2013.01); *A61B 3/0058* (2013.01); *A61B 3/14* (2013.01); *G06T 7/0024* (2013.01); *A61B 3/1233* (2013.01); *G06T 2207/30041* (2013.01); *G06T 2207/30096* (2013.01)

(58) Field of Classification Search
CPC ............. A61B 3/14; A61B 3/12; A61B 6/032
USPC .......................................... 351/206, 246, 205
See application file for complete search history.

(56) References Cited

U.S. PATENT DOCUMENTS

2010/0290005 A1* 11/2010 Huang ................. A61B 3/0058
351/206

FOREIGN PATENT DOCUMENTS

| JP | 2003-019158 A | 1/2003 |
|---|---|---|
| JP | 2011-255045 A | 12/2011 |
| KR | 10-2000-0022509 A | 4/2000 |
| KR | 10-2002-0059633 A | 7/2002 |

OTHER PUBLICATIONS

International Search Report for PCT/KR2013/006326 mailed on Oct. 28, 2013.

* cited by examiner

*Primary Examiner* — Hung Dang

(57) ABSTRACT

The present invention relates to an ophthalmic apparatus and to a treatment site measuring method for the apparatus. The ophthalmic apparatus according to the present invention comprises: a first image unit for capturing the lower region of a retina so as to generate an image of the captured retina; a second image unit for capturing the local region of the retina indicated by a surgical operator so as to generate an image of the captured local region of the retina; and a control unit for mapping the image of the local region of the retina generated by the second image unit to the image of the retina generated by the first image unit based on the image of the retina generated by the first image unit.

16 Claims, 5 Drawing Sheets

OPHTHALMIC APPARATUS, AND TREATMENT SITE MEASURING METHOD FOR THE APPARATUS

BACKGROUND OF THE INVENTION

1. Field of the invention

The present invention relates to an ophthalmic apparatus and methods of measuring, by the ophthalmic apparatus, a treatment location and, more particularly, to an ophthalmic apparatus for measuring a lesion location of an eyeball and methods of measuring, by the ophthalmic apparatus, a treatment location.

2. Related Art

Types of ocular diseases include diseases, such as glaucoma in which intraocular pressure rises in the vitreous humour of an eyeball, a cataract in which a whitening phenomenon is generated in the crystalline lens, and macular degeneration generated in a retinal image that is focused.

Recently, in order to treat ocular diseases, such as those described above, an ophthalmic treatment apparatus using a laser as a beam for treatment has emerged and the usability of the ophthalmic treatment apparatus is increasing. In order to treat ocular diseases using such an ophthalmic treatment apparatus, the treatment location of an ocular disease must be accurately measured. In particular, if a disease is generated in the retina, more accurate measurement is required because the retina is placed at the deepest location of an eyeball and includes many blood vessel, etc.

Meanwhile, a conventional ophthalmic apparatus is disclosed in "Korean Patent Application Publication No. 2000-0022509" entitled "Medical Laser Guidance Apparatus." The "medical laser guidance apparatus", that is, the aforementioned prior document, is technically characterized in that it includes retina image acquisition means, retina image display means for displaying a retinal image, reference data reception means for receiving data related to performed treatment from an operator when the data is used, template generation means for generating a reference template on a retinal image, target location reception means for receiving data related to at least one target point to which light is applied based on received reference data, current retina location detection means for outputting a signal indicative of the current location of the retina within the template based on a comparison between a current image of the retina from the retina image acquisition means and the template and the reference data, and laser light application means for directing laser light to the retina based on output from the current retina location detection means and the target location reception means.

However, the technical characteristic disclosed in the conventional prior document may have a problem in that it is difficult to measure a more accurate location of the retina because it uses a method of displaying a retinal image without photographing the fundus oculi region of the retina. Furthermore, an image recognized by an operator through a view finder is limited to a local portion of a retinal image, which makes it difficult to check that a location viewed through the view finder corresponds to which location of the entire retina. Accordingly, if an operator lacks of experience, it is frequently difficult to move a visual field of the view finder to an operation location.

SUMMARY OF THE INVENTION

An object of the present invention is to provide an ophthalmic apparatus having an improved structure and method for associating the fundus oculi region of the retina with a local region of the retina viewed by an operator so that the operator can easily secure the visual field of a treatment location and methods of measuring, by the ophthalmic apparatus, a treatment location.

According to the present invention, means for solving the object is accomplished by an ophthalmic apparatus measuring a treatment location of the retina, including a first image unit which performs photographing up to a lower region of the retina and generates a captured image of the retina, a second image unit which photographs a local region of the retina viewed by an operator and generates a captured image of the local region of the retina, and a control unit which maps the image of the local region of the retina generated by the second image unit to the image of the retina generated by the first image unit based on the image of the retina generated by the first image unit.

In this case, the ophthalmic apparatus may further include an image analysis unit which analyzes the image of the retina generated by the first image unit and a memory unit which stores the image of the retina analyzed by the image analysis unit.

The image analysis unit preferably may analyze a specific region of the image of the retina and send the analyzed region to the memory unit.

The specific region of the image of the retina may include macula flava.

Furthermore, the ophthalmic apparatus may further include a display unit which displays the image of the retina and the image of the local region of the retina generated by the first image unit and the second image unit.

Grids preferably may be displayed in the image of the retina displayed on the display unit. The image of the local region of the retina preferably may be mapped to a corresponding grid region of the image of the retina.

The first image unit may include a fundus oculi image unit which captures and generates the image of the retina.

In contrast, the second image unit may include a view finder viewed by an operator.

Meanwhile, according to the present invention, means for solving the object is also accomplished by a method of measuring, by the ophthalmic apparatus measuring a treatment location of the retina, a treatment location, including steps of (a) generating an image of a fundus oculi region of the retina by photographing the fundus oculi region of the retina, (b) generating an image of a local region of the retina by photographing the local region of the retina viewed by an operator, and (c) mapping the image of the local region of the retina to a location corresponding to the image of the fundus oculi region of the retina based on the image of the fundus oculi region of the retina.

In this case, the ophthalmic apparatus may include an image analysis unit which analyzes the fundus oculi region of the retina. The step (a) may include analyzing and extracting, by the image analysis unit, a specific region of the fundus oculi region of the retina.

The ophthalmic apparatus may include a memory unit which stores the image of the fundus oculi region of the retina analyzed by the image analysis unit. A step of storing information about the specific region analyzed by the image analysis unit may be further included between the step (a) and the step (b).

The information about the specific region may include at least one of macula flava and blood vessel locations of the retina.

Furthermore, the ophthalmic apparatus may further include a display unit which displays the image of the fundus oculi region of the retina and the image of the local region of the retina.

Furthermore, the step (c) may include a step of displaying grids in the image of the fundus oculi region of the retina displayed on the display unit and mapping the image of the local region of the retina to a corresponding grid region location in the image of the fundus oculi region of the retina.

Furthermore, the ophthalmic apparatus may further include a fundus oculi image unit which captures and generates the image of the fundus oculi region of the retina.

The ophthalmic apparatus may further include a view finder which captures and generates the image of the local region of the retina in the step (b).

The details of other embodiments are included in the detailed description and the drawings.

The ophthalmic apparatus and the methods of measuring, by the ophthalmic apparatus, a treatment location according to the present invention are advantageous in that an accurate treatment location of an eyeball on which an operator wants to perform a treatment process can be measured because an image of a local region of the retina viewed by the operator and generated by the second image unit can be mapped to an image of the retina generated by the first image unit.

DESCRIPTION OF EXEMPLARY EMBODIMENTS

Hereinafter, an ophthalmic apparatus and methods of measuring a treatment location using the same in accordance with embodiments of the present invention are described in detail with reference to the accompanying drawings.

Figure 1:
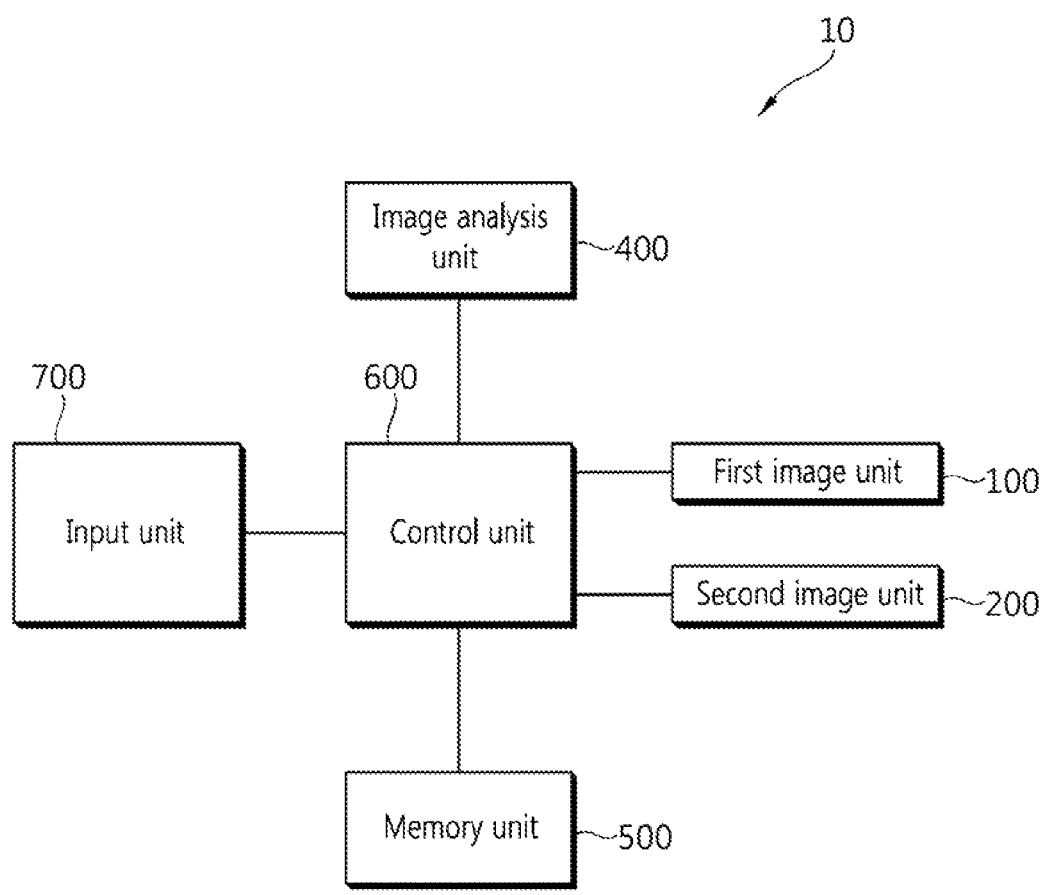
FIG. 1 is a control block diagram of an ophthalmic apparatus in accordance with embodiments of the present invention.

FIG. 1 is a control block diagram of an ophthalmic apparatus in accordance with embodiments of the present invention.

As illustrated in FIG. 1, the ophthalmic apparatus 10 in accordance with embodiments of the present invention includes a first image unit 100, a second image unit 200, a display unit 300, an image analysis unit 400, a memory unit 500, a control unit 600, and an input unit 700.

The first image unit 100 performs photographing up to a lower region of the retina and generates a captured image of the retina. The first image unit 100 includes a fundus oculi image unit and photographs and generates an image F (refer to FIGS. 2 and 4) of the fundus oculi region of the retina.

The second image unit 200 photographs a local region of the retina that may be checked by an operator through a view finder and generates an image L (refer to FIGS. 2 and 4) of the local region. The second image unit 200 is installed adjacent to the view finder for enabling an operator to view a local region of the retina and installed so that the optical axis of the view finder may be shared. The second image unit 200 photographs the image L of the local region that is viewed by an operator. In this case, a known photographing unit, such as a digital camera, may be applied to the view finder provided as the second image unit 200.

The display unit 300 (refer to FIGS. 2 and 4) displays the image F of the fundus oculi region of the retina and the image L of the local region of the retina generated by the first image unit 100 and the second image unit 200 so that an operator may view the images F and L. The display unit 300 is provided as a known image device, such as a liquid crystal display device.

Meanwhile, grids G (refer to FIGS. 2 and 4) may be displayed in the image F of the fundus oculi region of the retina, generated by the first image unit 100, on the display unit 300. As described above, the image L of the local region of the retina viewed by an operator is mapped to a corresponding location in the image F of the fundus oculi region of the retina displayed on the display unit 300.

Next, the image analysis unit 400 analyzes the image F of the fundus oculi region of the retina generated by the first image unit 100. The image analysis unit 400 analyzes a specific region of the image F of the fundus oculi region of the retina in order to map the image L of the local region of the retina to the image F of the fundus oculi region of the retina. In this case, the specific region of the image F of the fundus oculi region of the retina that is analyzed by the image analysis unit 400 may include the macula flava, blood vessel location, and blood vessel shape of the retina. The image analysis unit 400 sends information about a specific region of the image F of the fundus oculi region of the retina to the memory unit 500.

The memory unit 500 stores the specific region of the image F of the fundus oculi region of the retina that has been transmitted by the image analysis unit 400. Furthermore, the memory unit 500 also stores the image F of the fundus oculi region of the retina generated by the first image unit 100 and the image L of the local region of the retina generated by the second image unit 200. Information stored in the memory unit 500 is transmitted to the control unit 600.

The control unit 600 generates a control signal such that the image L of the local region of the retina generated by the second image unit is mapped to the image F of the fundus oculi region of the retina based on the image F of the fundus oculi region of the retina generated by the first image unit 100. Such a mapping method is described in detail. The control unit 600 maps the image L of the local region of the retina to the image F of the fundus oculi region of the retina using information about the specific region of the image F of the fundus oculi region of the retina that has been stored in the memory unit 500. In this case, if the image L of the local region includes an image of a specific region, the image L of the local region of the retina may be mapped to the image F of the fundus oculi region of the retina using a correlation between the image of the specific region of the image F of the fundus oculi and the image of the specific region of the image L of the local region. If the image L of the local region does not include an image of a specific region, the image L of the local region of the retina may be mapped to the image F of the fundus oculi region of the retina using a correlation between an image at a location where the specific region of the image of the fundus oculi has not been formed and the image L of the local region.

In this case, the control unit 600 may display the grids G in the image F of the fundus oculi region of the retina displayed on the display unit 300 in order to further improve the mapping of the image L of the local region of the retina to the image F of the fundus oculi region of the retina.

If the image L of the local region currently viewed by an operator through the view finder is found to correspond to which location of the entire image of the fundus oculi as described above, the operator can easily move the visual field of the view finder to a treatment location T based on the found location.

In this case, the input unit 700 may provide an input signal from which the view finder may move to a location where the image L of the local region of the retina is mapped to the image F of the fundus oculi region of the retina. This input unit may enable a user to manually display moving coordinates in the X axis and the Y axis for moving a current location to a treatment location (target location) on the display unit using a lever or a joystick. If an operator's check is present, this input unit may input an input signal so that a current location automatically moves to a treatment location.

<First Embodiment>

Figure 2:
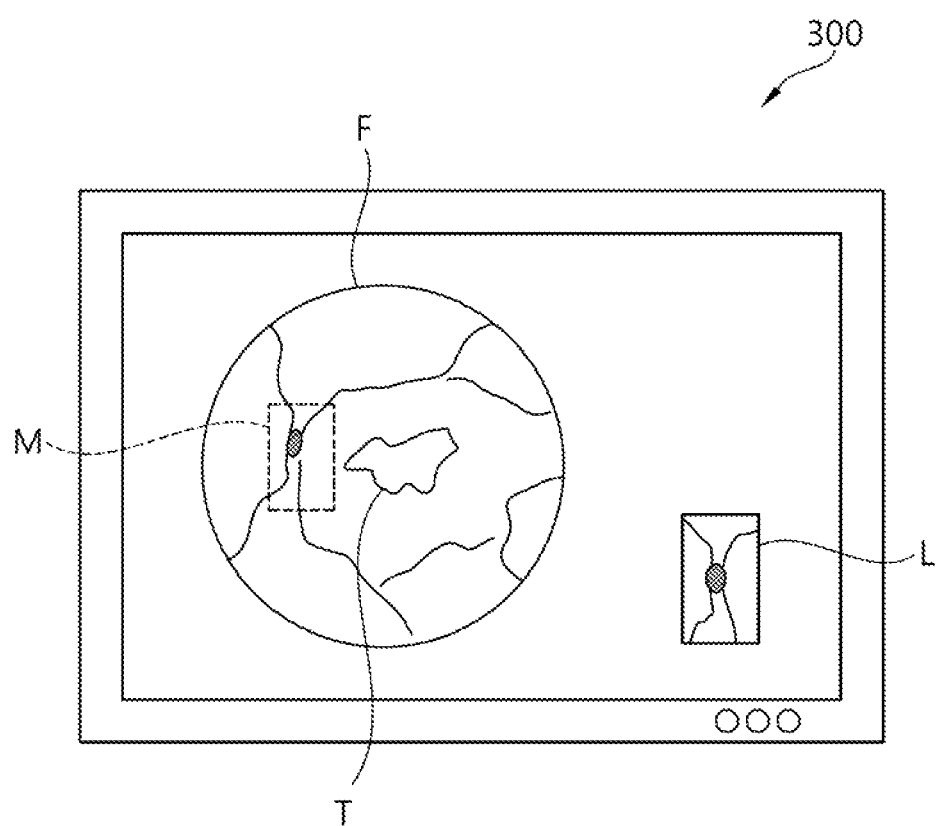
FIG. 2 is a schematic configuration in which images formed by the first image unit and second image unit of the ophthalmic apparatus are displayed in accordance with a first embodiment of the present invention.
Figure 3:
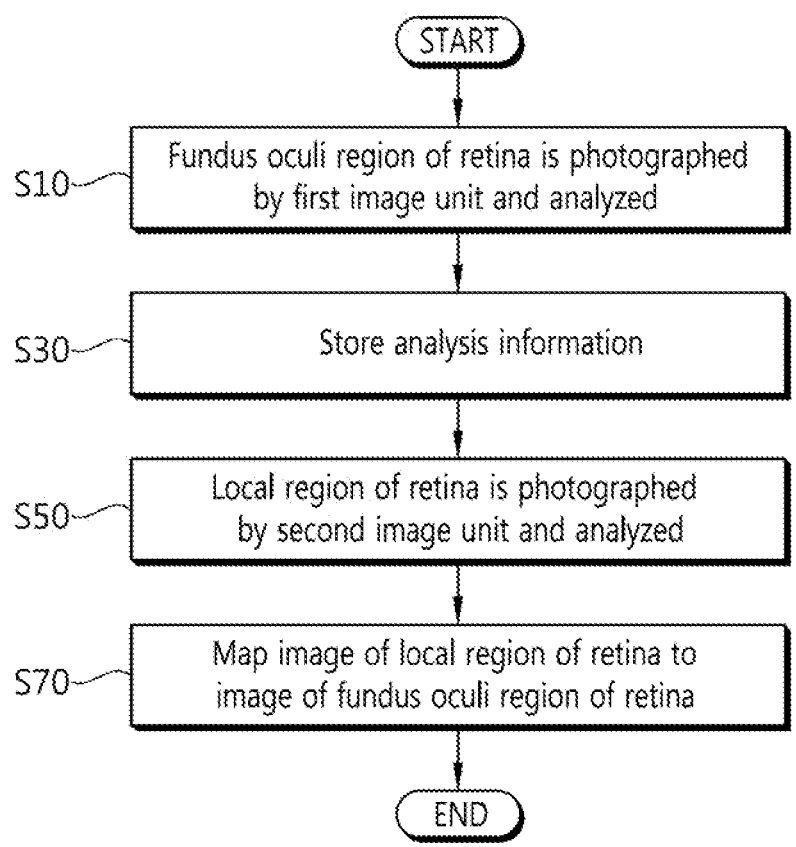
FIG. 3 is a control flowchart illustrating a method of measuring, by the ophthalmic apparatus, a treatment location in accordance with a first embodiment of the present invention.

FIG. 2 is a schematic configuration in which images formed by the first image unit and second image unit of the ophthalmic apparatus are displayed in accordance with a first embodiment of the present invention, and FIG. 3 is a control flowchart illustrating a method of measuring, by the ophthalmic apparatus, a treatment location in accordance with a first embodiment of the present invention.

As illustrated in FIG. 2, the image F of the fundus oculi region of the retina captured and generated by the first image unit 100 is displayed on the display unit 300. Furthermore, the image L of the local region of the retina captured and generated by the second image unit 200 is displayed on the display unit 300 along with the image F of the fundus oculi region of the retina.

In this case, information about a specific region of the image F of the fundus oculi region of the retina displayed on the display unit 300 is analyzed by the image analysis unit 400 and transmitted to the memory unit 500. The control unit 600 maps the image L of the local region of the retina to a mapping location M in the image F of the fundus oculi region of the retina based on the information transmitted to the memory unit 500.

The method of measuring, by the ophthalmic apparatus 10 configured as described above, a treatment location in accordance with the first embodiment of the present invention is described below with reference to FIG. 3.

First, the first image unit 100 operates and generates the image F of a fundus oculi region of the retina by photographing the fundus oculi region of the retina. The generated image F of the fundus oculi region of the retina is analyzed (S10). Information about a specific region of the image F of the fundus oculi region of the retina analyzed by the image analysis unit 400 at step 'S10' is stored in the memory unit 500 (S30).

The second image unit 200 generates the image L of a local region of the retina by photographing the local region of the retina that is viewed by an operator (S50). The image L of the local region of the retina is mapped to the mapping location M in the image F of the fundus oculi region of the retina using the information stored in the memory unit 500.

<Second Embodiment>

Figure 4:
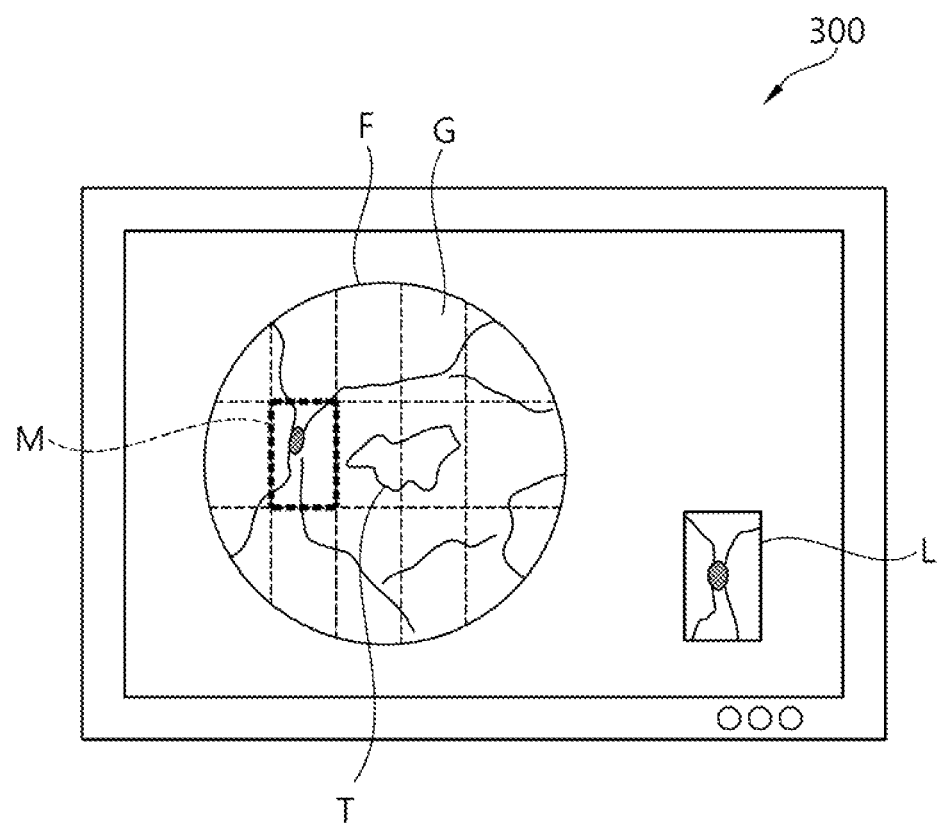
FIG. 4 is a schematic configuration in which images formed by the first image unit and second image unit of the ophthalmic apparatus are displayed in accordance with a second embodiment of the present invention.
Figure 5:
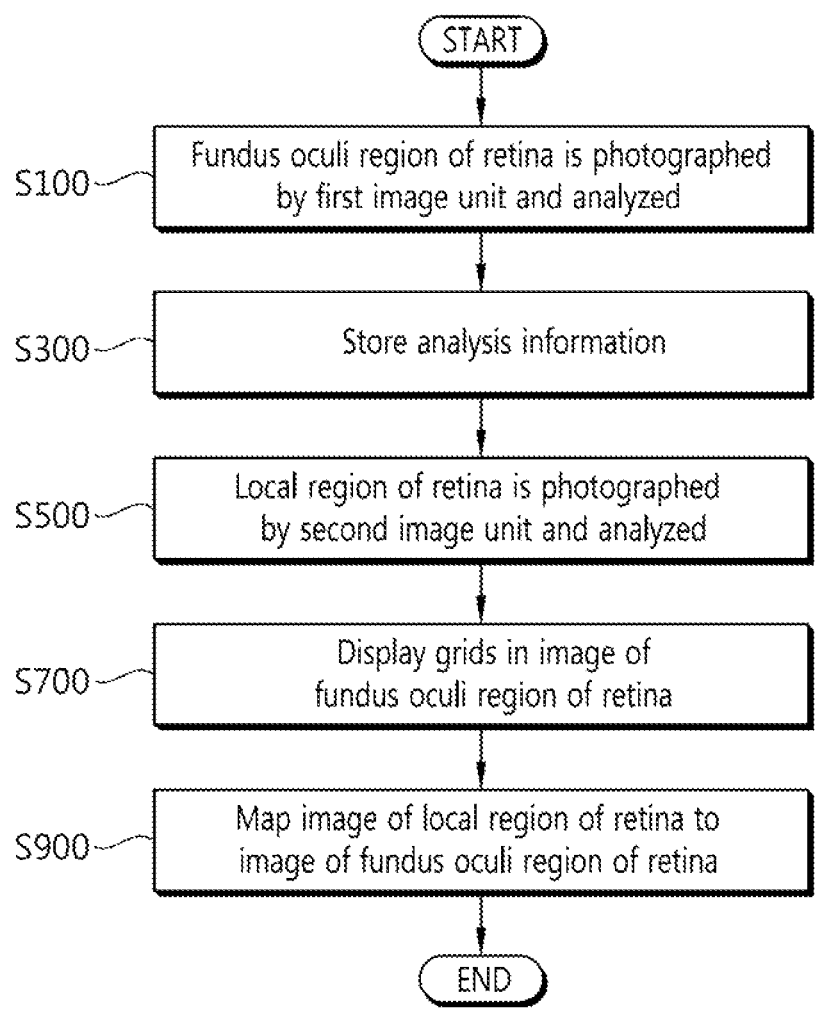
FIG. 5 is a control flowchart illustrating a method of measuring, by the ophthalmic apparatus, a treatment location in accordance with a second embodiment of the present invention.

FIG. 4 is a schematic configuration in which images formed by the first image unit and second image unit of the ophthalmic apparatus are displayed in accordance with a second embodiment of the present invention, and FIG. 5 is a control flowchart illustrating a method of measuring, by the ophthalmic apparatus, a treatment location in accordance with a second embodiment of the present invention.

As illustrated in FIG. 4, the image F of the fundus oculi region of the retina captured and generated by the first image unit 100 is displayed on the display unit 300. Furthermore, the image L of the local region of the retina captured and generated by the second image unit 200 is displayed on the display unit 300 along with the image F of the fundus oculi region of the retina.

In this case, a specific region of the image F of the fundus oculi region of the retina displayed on the display unit 300 is analyzed by the image analysis unit 400 and transmitted to the memory unit 500. Meanwhile, the grids G are displayed in the image F of the fundus oculi region of the retina, displayed on the display unit 300, around the mapping location M. The control unit 600 maps the image L of the local region of the retina to the mapping location M in the image F of the fundus oculi region of the retina based on the information stored in the memory unit 500 and the grids G displayed in the image F of the fundus oculi region of the retina.

The method of measuring, by the ophthalmic apparatus 10 configured as described above, a treatment location in accordance with the second embodiment of the present invention is described below with reference to FIG. 5.

First, the first image unit 100 operates and generates the image F of the fundus oculi region of the retina by photographing the fundus oculi region of the retina. The generated image F of the fundus oculi region of the retina is analyzed (S100). Information about a specific region of the image F of the fundus oculi region of the retina analyzed by the image analysis unit 400 at step 'S100' is stored in the memory unit 500 (S300).

The second image unit 200 generates the image L of a local region of the retina by photographing the local region of the retina viewed by an operator (S500). The grids G are displayed in the image F of the fundus oculi region of the retina in order to improve efficiency of the mapping of the image L of the local region of the retina to the mapping location M in the image F of the fundus oculi region of the retina.

The image L of the local region of the retina is mapped to the mapping location in the image F of the fundus oculi region of the retina based on the information stored in the memory unit 500 and the grids G displayed in the image F of the fundus oculi region of the retina.

As described above, an accurate treatment location of an eyeball on which an operator wants to perform a treatment process can be measured because an image of a local region of the retina viewed by the operator and generated by the second image unit can be mapped to an image of the retina generated by the first image unit.

As described above, although the embodiments of the present invention have been described with reference to the accompanying drawings, those skilled in the art to which the present invention pertains will understand that the present invention may be implemented in other detailed forms without changing the technical spirit or indispensable characteristics of the present invention. Accordingly, it will be understood that the aforementioned embodiments are illustrative and not limitative from all aspects. The scope of the present invention is defined by the appended claims rather than the detailed description, and the present invention should be construed as covering all modifications or variations derived from the meaning and scope of the appended claims and their equivalents.

What is claimed is:

1. An ophthalmic apparatus measuring a treatment location of a retina, comprising:
   a first image unit which performs photographing up to a lower region of the retina and generates a captured image of the retina;
   a second image unit which photographs a local region of the retina viewed by an operator and generates a captured image of the local region of the retina; and
   a control unit which maps the image of the local region of the retina generated by the second image unit to the image of the retina generated by the first image unit based on the image of the retina generated by the first image unit.

2. The ophthalmic apparatus of claim 1, further comprising:
   an image analysis unit which analyzes the image of the retina generated by the first image unit; and
   a memory unit which stores the image of the retina analyzed by the image analysis unit.

3. The ophthalmic apparatus of claim 2, wherein the image analysis unit analyzes a specific region of the image of the retina and sends the analyzed region to the memory unit.

4. The ophthalmic apparatus of claim 3, wherein the specific region of the image of the retina comprises macula flava.

5. The ophthalmic apparatus of claim 2, further comprising a display unit which displays the image of the retina and the image of the local region of the retina generated by the first image unit and the second image unit.

6. The ophthalmic apparatus of claim 5, wherein:
   grids are displayed in the image of the retina displayed on the display unit, and
   the image of the local region of the retina is mapped to a corresponding grid region of the image of the retina.

7. The ophthalmic apparatus of claim 5, wherein the first image unit comprises a fundus oculi image unit which captures and generates the image of the retina.

8. The ophthalmic apparatus of claim 5, wherein the second image unit comprises a view finder viewed by an operator.

9. A method of measuring, by an ophthalmic apparatus measuring a treatment location of a retina, a treatment location, the method comprising steps of:
   (a) generating an image of a fundus oculi region of the retina by photographing the fundus oculi region of the retina;
   (b) generating an image of a local region of the retina by photographing the local region of the retina viewed by an operator; and
   (c) mapping the image of the local region of the retina to a location corresponding to the image of the fundus oculi region of the retina based on the image of the fundus oculi region of the retina.

10. The method of claim 9, wherein:
    the ophthalmic apparatus comprises an image analysis unit which analyzes the fundus oculi region of the retina, and
    the step (a) comprises analyzing and extracting, by the image analysis unit, a specific region of the fundus oculi region of the retina.

11. The method of claim 10, wherein:
    the ophthalmic apparatus comprises a memory unit which stores the image of the fundus oculi region of the retina analyzed by the image analysis unit, and
    a step of storing information about the specific region analyzed by the image analysis unit is further included between the step (a) and the step (b).

12. The method of claim 11, wherein the information about the specific region comprises at least one of macula flava and blood vessel locations of the retina.

13. The method of claim 10, wherein the ophthalmic apparatus further comprises a display unit which displays the image of the fundus oculi region of the retina and the image of the local region of the retina.

14. The method of claim 13, wherein the step (c) comprises a step of displaying grids in the image of the fundus oculi region of the retina displayed on the display unit and mapping the image of the local region of the retina to a corresponding grid region location in the image of the fundus oculi region of the retina.

15. The method of claim 13, wherein the ophthalmic apparatus further comprises a fundus oculi image unit which captures and generates the image of the fundus oculi region of the retina.

16. The method of claim 13, wherein the ophthalmic apparatus further comprises a view finder which captures and generates the image of the local region of the retina in the step (b).

* * * * *